(12) United States Patent
Alcade et al.

(10) Patent No.: US 7,045,630 B2
(45) Date of Patent: May 16, 2006

(54) METHOD FOR PREPARING 4-AMINO-4-PHENYLPIPERIDINES

(75) Inventors: Alain Alcade, Toulouse (FR); Gilles Anne-Archard, Toulouse (FR); Daniel Capraro, Portet sur Garonne (FR)

(73) Assignee: Sanofi-aventis, Paris (FR)

( * ) Notice: Subject to any disclaimer, the term of this patent is extended or adjusted under 35 U.S.C. 154(b) by 95 days.

(21) Appl. No.: 10/483,532

(22) PCT Filed: Jul. 15, 2002

(86) PCT No.: PCT/FR02/02499

§ 371 (c)(1),
(2), (4) Date: Jan. 12, 2004

(87) PCT Pub. No.: WO03/008382

PCT Pub. Date: Jan. 30, 2003

(65) Prior Publication Data

US 2004/0171837 A1    Sep. 2, 2004

(30) Foreign Application Priority Data

Jul. 16, 2001 (FR) .................................. 01 09576

(51) Int. Cl.
*C07D 211/56* (2006.01)
*C07D 211/98* (2006.01)
*C07D 211/08* (2006.01)

(52) U.S. Cl. ................ 546/215; 546/244; 546/192
(58) Field of Classification Search ............... 546/215, 546/244, 192
See application file for complete search history.

(56) References Cited

U.S. PATENT DOCUMENTS 3,311,624 A    3/1967    Ohnacker et al.

FOREIGN PATENT DOCUMENTS

WO    WO01/07050    2/2001
WO    WO 01/07050   2/2001

OTHER PUBLICATIONS

Marco et al, Tetrahedron, vol. 55, pp. 7625-7644, 1999.*
Giardina et al, Bioorganic & Medicinal Chemistry Letters, vol. 6, No. 19, pp. 2307-2310, 1996.*
Iorio, M.A. et al., Farmaco, Edizione Scientifica, Societa Chimica Italiana, Pavia, IT, vol. 39, No. 7, pp. 599-611 (1984).
Hermans, Bert et al., J. Med. Chem., pp. 851-855 (1965).
Westeringh et al., J. Med. Chem., pp. 619-623 (1964).
M.A. Iorio, et al., Nitrogen Analogues Of Phencyclidine: 1-Alkyl-4-Phenyl-4-(1-Piperidinyl)Piperidines, Farmaco Edizione Scientifica, Societa Chimica Italiana, Pavia, IT (1984, pp. 599-611, vol. 39).
Bert Hermans, et al., 4-Substituted Piperidines. II. Reaction of 1-Benzyl-4-Cyano-4-t-aminopiperidines with Organometallic Compounds, J. Med. Chem. (1965, pp. 851-855, vol. 8).
Cornelis Van De Westeringh, et al., 4-Substituted Piperidines. I. Derivatives of 4-t-Amino-4-Piperidinecarboxamides, J. Med. Chem. (1964, pp. 619-623, vol. 7).

* cited by examiner

*Primary Examiner*—D. Margaret Seaman
*Assistant Examiner*—Niloofar Rahmani
(74) *Attorney, Agent, or Firm*—Balaram Gupta

(57) ABSTRACT

The invention relates to a process for preparing a 4-amino-4-phenylpiperidine (I):

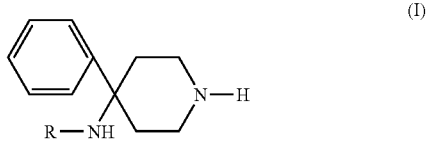

in which R is hydrogen or a $(C_1-C_3)$alkyl group, characterized in that a 1-protected 4-piperidone (II):

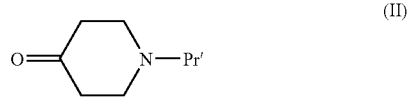

in which Pr' represents a removable N-protecting group, is treated sequentially first with an alkali metal cyanide and then with an amine ENHPr" (III) in which E represents a group R'=$(C_1-C_3)$alkyl, or an N-protecting group and Pr" is an N-protecting group, the protecting group(s) being removable under the same conditions as Pr'; then the compound thus obtained (IV) is subjected to a Grignard reaction with a phenylmagnesium halide, the two or three protecting groups are removed from the compound thus obtained (V) and compound (I) is isolated or in the form of the free base, which is converted into one of its salts.

16 Claims, No Drawings

METHOD FOR PREPARING 4-AMINO-4-PHENYLPIPERIDINES

The present invention relates to a process for preparing 4-amino-4-phenylpiperidine and salts thereof. These compounds are useful as intermediates for the preparation of pharmaceutical active principles, for example osanetant.

G.A.M. Giardina et al. (Bioorg. Med. and Chem. Letters, 1996, 6, 2307–2310) describe a synthesis of 4-methylamino-4-phenylpiperidine of formula (C):

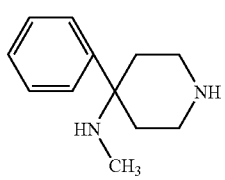

(C)

in six steps from 1-benzyl-4-piperidone via reaction with phenyllithium, treatment of the 1-benzyl-4-phenylpiperidin-4-ol thus obtained with sulfuric acid and acetic acid in acetonitrile, deacetylation of the 4-acetamido-1-benzyl-4-phenylpiperidine, N-formulation of the 4-amino-1-benzyl-4-phenylpiperidine, reduction of the N-formyl derivative thus obtained with lithium aluminum hydride and final debenzylation of the 1-benzyl-4-methylamino-4-phenylpiperidine via catalytic hydrogenation.

Although these six steps proceed in good yields, the process has drawbacks that make it difficult to apply industrially. More particularly, in the preparation of compound (C), two of the six steps are performed at reflux for three days which considerably lengthens the duration of the process. Furthermore, the preparation of compound (C) involves, in the first step, the use of phenyllithium, which may entail appreciable problems at the industrial level.

It has now been found that, starting with 1-benzyl-4-piperidone or, generally, with 1-protected 4-piperidone, it is possible to prepare 4-methylamino-4-phenylpiperidine (compound C above) in only four steps, the first two of which may optionally be performed one after the other in the same reactor ("one-pot" reaction), starting with cyanohydrin, a reaction with benzylmethylamine (or, more generally, N-protected methylamine), a reaction with phenylmagnesium bromide and a deprotection of the nitrogen atoms of piperidine and of the methylamine in position 4 of the piperidine.

It has also been found that by replacing the N-protected methylamine with another N-protected alkylamine, other 4-alkylamino-4-phenylpiperidines may be prepared, the synthesis of which is not possible using the method proposed by G.A.M. Giardina et al. in the document mentioned above.

It has especially been found that by working via the cyanohydrin and its product of reaction with the amine, followed by a Grignard reaction, the reaction conditions and the protecting groups for the two nitrogen atoms may be selected so as to proceed via suitable intermediates. Consequently, the process via the cyanohydrin and the Grignard reagent makes it possible to prepare variously substituted 4-amino-4-phenylpiperidines.

More particularly, it has been found that by replacing benzylmethylamine (or, more generally, the N-protected methylamine) with dibenzylamine (or, more generally, ammonia substituted with two N-protecting groups), 4-amino-4-phenylpiperidine, optionally 4-N-protected, is obtained very simply.

Thus, according to one of its aspects, a subject of the present invention is a process for preparing a 4-amino-4-phenylpiperidine of formula (I)

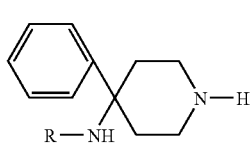

(I)

in which R is hydrogen or a $(C_1-C_3)$alkyl group, characterized in that:
(a) a 1-protected 4-piperidone of formula

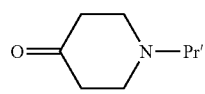

(II)

in which Pr' represents a removable N-protecting group, is treated sequentially first with an alkali metal cyanide and then, in the reaction medium containing the cyanohydrin thus obtained, with an amine of formula:

(III)

in which E represents a group $R'=(C_1-C_3)$alkyl, or an N-protecting group, the protecting group(s) being removable under the same conditions as Pr';
(b) the compound thus obtained of formula:

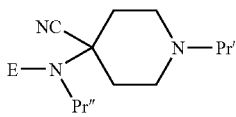

(IV)

in which Pr', Pr" and E are as defined above, is subjected to a Grignard reaction with a phenylmagnesium halide; and
(c) the two or three N-protecting groups are removed from the compound thus obtained of formula:

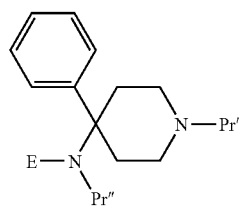

(V)

and compound (I) is isolated either in the form of one of its salts, which is converted into the free base, or in the form of the free base, which is converted into one of its salts.

In step (a), the process is performed under the usual conditions for forming cyanohydrins, advantageously using potassium cyanide as alkali metal cyanide and a compound of formula (II) in which Pr' is a benzyl radical, which is unsubstituted or substituted on the benzene ring with a halogen, a $(C_1-C_4)$alkyl group or a $(C_1-C_4)$alkoxy group; a benzhydryl radical; or a trityl radical, preferably a benzyl radical.

After removing the aqueous phase, the reaction mixture, in an aqueous-organic solvent, preferably in a water/toluene or water/ethanol mixture, is treated directly with the compound of formula (III). A compound of formula (III) in which Pr" is a benzyl radical, which is unsubstituted or substituted on the benzene ring with a halogen, a $(C_1-C_4)$ alkyl group, a $(C_1-C_4)$alkoxy group; a benzhydryl radical or a trityl radical, preferably a benzyl radical, is advantageously used.

In compound (III), E is advantageously $(C_1-C_3)$alkyl, preferably methyl.

In compound (III), E may also be an N-protecting group such as a benzyl radical, which is unsubstituted or substituted on the benzene ring with a halogen, a $(C_1-C_4)$alkyl or a $(C_1-C_4)$alkoxy; a benzhydryl radical or a trityl radical, preferably a benzyl radical.

The process is then performed in the solvent, advantageously in toluene in the presence of magnesium sulfate, or in a water/ethanol mixture. Under these conditions, after 2 to 12 hours at a temperature of from 30 to 45° C., the reaction is complete and the compound of formula (IV) is isolated according to the conventional techniques:
  for example by adding water and removing the byproducts by treatment with an acid, for example acetic acid, and a base, for example sodium hydroxide, removing the aqueous phase and evaporating off the organic solvent, advantageously toluene;
  or by crystallization from an ethanol/water mixture.

In step (b), the phenylmagnesium halide is prepared at the time of use from a halobenzene and magnesium. Preferably, phenylmagnesium bromide is prepared from bromobenzene and magnesium in a toluene/methyl tert-butyl ether or toluene/tetrahydrofuran mixture. A solution of the compound of formula (IV) in toluene is added to the solution containing the phenylmagnesium halide and, after 1–2 hours at room temperature, the complex thus formed is hydrolyzed and compound (V) is isolated according to the conventional methods, for example as illustrated above for the isolation of the compound of formula (IV). Compound (V) is isolated in the form of the free base or of one of its salts.

In step (c), the protecting groups Pr' and Pr" and optionally E are removed at the same time. When, in the compound of formula (V) thus obtained, Pr' and Pr" and optionally E are a benzyl radical, which is unsubstituted or substituted on the benzene ring with a halogen, a $(C_1-C_4)$alkyl group or a $(C_1-C_4)$alkoxy group; a benzhydryl radical; or a trityl radical, preferably a benzyl radical, the deprotection is readily performed via catalytic hydrogenation of said compound (V), in the form of the free base or of one of its salts. Advantageously, palladium-on-charcoal (Pd/C) is used as catalyst.

The compound of formula (I) is isolated in the form of the free base when the starting compound (V) was in free base form, or alternatively in the form of the same salt as that of the salified compound (V), when compound (V) subjected to the hydrogenation was in salt form. In the latter case, the free base may be obtained via neutralization.

In step (a), an amine of formula (III) in which E represents an N-protecting group is used to prepare a compound of formula (I) in which R is hydrogen. Preferably, an amine of formula (III) in which E represents a group $R'=(C_1-C_3)$alkyl is used in step a).

More particularly, the present invention also relates to a process for preparing the compounds of formula (I), in which R is other than hydrogen.

The compounds of formula (IV) and of formula (V), in which R' is as defined above and Pr' and Pr" are the advantageous radicals mentioned above and the salts thereof, are novel compounds that constitute the key intermediates of the process of the present invention.

Thus, according to another of its aspects, a subject of the present invention is the compounds of formula:

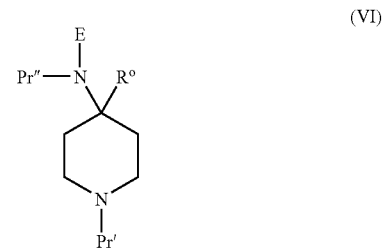

(VI)

in which E is a $(C_1-C_3)$alkyl, a benzyl radical, which is unsubstituted or substituted on the benzene ring with a halogen, a $(C_1-C_4)$alkyl or a $(C_1-C_4)$alkoxy; a benzhydryl radical or a trityl radical, $R^o$ is a cyano or phenyl group, Pr' and Pr", independently of each other, represent a benzyl radical, which is unsubstituted or substituted on the benzene ring with a halogen, a $(C_1-C_4)$alkyl or $(C_1-C_4)$alkoxy group; a benzhydryl radical; a trityl radical; and the salts thereof.

Among the compounds of formula (VI) that are preferred are those for which E is a $(C_1-C_3)$alkyl; the compounds for which E is methyl being particularly advantageous.

The compounds of formula (VI) in which Pr' and Pr" are both benzyl are also very advantageous, and, among these compounds:
  1-benzyl-4-[(N-benzyl)methylamino)]-4cyanopiperidine and its salts, and also
  1-benzyl-4-[(N-benzyl)methylamino]-4phenylpiperidine and its salts, especially the dioxalate, are preferred.

EXAMPLE 1

(a) An aqueous solution of 1-benzyl-4-piperidone hydrochloride (prepared from 221.6 g of 1-benzyl-4-piperidone, 60 g of ice, 60 ml of water and 100 ml of 36% HCl) is added with stirring, over 3 hours, to a mixture of 83.8 g of potassium cyanide, 100 ml of water and 750 ml of toluene, cooled to 15° C. The mixture thus obtained is heated to 45° C., while capturing the gases possibly evolved by neutralization, the aqueous phase is then removed after separation of the phases by settling, the toluene phase is cooled to 20° C. and 279 g of magnesium sulfate are added thereto, followed by addition, at 45° C., of 160 g of N-benzylmethylamine. After 6 hours at this temperature, 750 ml of water are gradually added at 40° C. Still at this temperature, the phases are separated by settling, the aqueous phase is removed and the organic phase is then cooled to 15° C. and 500 ml of water and 20 g of glacial acetic acid are added. The phases are separated by settling, the aqueous phase is removed, the organic phase is washed first with water and then with dilute sodium hydroxide and finally with water again, the toluene phase is dried azeotropically and evaporated to dryness under vacuum, and the solid residue is dried under vacuum at 40° C. 345.5 g of 1-benzyl-4-cyano-4-[(N-methyl)benzylamino]piperidine are thus obtained; m.p.=67–68° C.

(b) 330 g of the product obtained at the end of step (a) are added to 2.11 l of a solution of phenylmagnesium bromide in a toluene/methyl tert-butyl ether mixture obtained from 486.6 g of bromobenzene and 75.32 g of magnesium and cooled to 15° C. The reaction mixture is left for 2 hours at room temperature and is then treated with 1.5l of ice-cold water and 100 ml of aqueous 30% hydrogen peroxide solution for 90 minutes at 2° C., and stirred for 30 minutes. The phases are separated by settling, the aqueous phase is removed and the organic phase is washed with water. This phase is treated with a solution of 70 ml of acetic acid in 765 ml of water to obtain a pH of between 6.5 and 7.5. The organic phase is treated with dilute hydrochloric acid, and the aqueous phase is removed and treated with 1.5 l of n-butanol. Sodium hydroxide is added to pH 14, the phases are separated by settling and the organic phase is washed under hot conditions (60° C.) with water. The aqueous phase is removed and the organic phase is dried azeotropically. This phase is cooled to 70° C., 2.24 l of absolute ethanol are added followed by a solution of 185 g of oxalic acid in 180 ml of ethanol, and the mixture is refluxed for 1 hour. The resulting mixture is allowed to cool to 20° C. and the precipitate is filtered off and washed with ethanol. 382 g of 1-benzyl-4-(N-methyl)benzylamino-4-phenylpiperidine dioxalate are thus obtained; m.p.=179–180° C.

(c) A mixture of 300 g of the product obtained at the end of step (b), 1.5 l of methanol and 30 g of 5% Pd/C containing 50% water is hydrogenated at 45° C. and at ambient pressure for 24 hours, 300 ml of water are then added thereto and the mixture is refluxed for 30 minutes. The mixture is filtered at this temperature, the methanol is removed by distillation and the essentially aqueous phase is heated to 95° C. 1.7 l of n-butanol are added while maintaining the temperature at 95° C., the mixture is then refluxed and cooled to 20° C., and the precipitate is filtered off, washed with a 9/1 butanol/water mixture (v/v) and dried at 60° C. under vacuum. 144.25 g of 4-methylamino-4-phenylpiperidine sesquioxalate monohydrate are thus obtained; m.p.=252–254° C. (capillary).

EXAMPLE 2

(a) An aqueous solution of 1-benzylpiperidin-4-one hydrochloride (prepared from 110.8 g of 1-benzyl-4-piperidone, 30 ml of water, 30 g of ice and 50 ml of 36% HCl) is added with stirring, over 3 hours, to a mixture of 41.9 g of potassium cyanide, 50 ml of water and 380 ml of toluene, cooled to 15° C. The mixture thus obtained is heated to 45° C. while capturing the gases possibly evolved by neutralization, the aqueous phase is then discarded, the toluene phase is cooled to 20° C. and 140 g of magnesium sulfate are added, followed by addition, at 45° C., of 90.7 g of N-benzylethylamine. After 10 hours at this temperature, 380 ml of water are gradually added, at 40° C., the phases are separated by settling at the same temperature, the aqueous phase is removed and the organic phase is then cooled to 15° C., and 250 ml of water and 10 g of glacial acetic acid are added. The aqueous phase is removed and the organic phase is washed with water, then with dilute sodium hydroxide and finally again with water. The toluene phase is dried azeotropically and evaporated to dryness, and the solid residue is dried at 40° C. under vacuum. 193.2 g of 1-benzyl-4-cyano-4-[(N-ethyl)benzylamino]piperidine are thus obtained.

(b) 193 g of the product obtained at the end of step (a) are added to 1.05 l of a solution of phenylmagnesium bromide in a toluene/methyl tert-butyl ether mixture, obtained from 243.3 g of bromobenzene and 37.66 g of magnesium and cooled to 15° C. The mixture is left for 2 hours at room temperature and is then treated for 75 minutes at −2° C with 750 ml of icecold water and 50 ml of aqueous 30% hydrogen peroxide solution. The mixture thus obtained is stirred for 30 minutes. It is treated with a solution of 35 ml of acetic acid in 380 ml of water to obtain a pH of between 6.5 and 7.5. The aqueous phase is removed and the organic phase is washed with water. The organic phase is treated with dilute hydrochloric acid and removed. The aqueous phase is treated with 750 ml of n-butanol and then with sodium hydroxide solution to pH 14. The aqueous phase is separated out by settling of the phases, the organic phase is washed with water at 60° C. and the aqueous phase is then removed and the butanol solution is dried azeotropically. 1.1 l of absolute ethanol are added at 65–70° C., followed by addition, at the same temperature, of a solution of 92.5 g of oxalic acid in 90 ml of ethanol. The mixture is refluxed for 30 minutes and then cooled and the precipitate is filtered off and washed with cold ethanol. 196.5 g of 1-benzyl-4-(N-ethyl)benzylamino-4-phenylpiperidine dioxalate are thus obtained.

(c) A mixture of 150 g of the product obtained at the end of step (b), 750 ml of methanol and 15 g of 5% Pd/C containing 50% water is hydrogenated at 45° C. and at ambient pressure for 24 hours, 150 ml of water are added thereto and the mixture is refluxed for 30 minutes. The mixture is filtered at this temperature and the methanol and water are removed by distillation. The solid residue is taken up in 2.5 l of acetone and the pH is adjusted to 2.5–3 with oxalic acid. This mixture is stirred for 2 hours at room temperature and the precipitate is filtered off, washed with acetone and dried at 60° C. under vacuum. 85.7 g of 4-ethylamino-4-phenylpiperidine dioxalate are thus obtained.

EXAMPLE 3

(a) An aqueous solution of 1-benzyl-4-piperidone hydrochloride (prepared from 221.6 g of 1-benzyl-4-piperidone, 60 g of ice, 60 ml of water and 100 ml of 36% HCl) is added with stirring, over 3 hours, to a mixture of 83.8 g of potassium cyanide, 100 ml of water and 750 ml of toluene, cooled to 15° C. The mixture thus obtained is heated to 45° C., while capturing the gases possibly evolved by neutralization, the aqueous phase is then removed after separation of the phases by settling, the toluene phase is cooled to 20° C. and 279 g of magnesium sulfate are added thereto, followed by addition, at 45° C., of 160 g of N-benzylmethylamine. After 6 hours at this temperature, 750 ml of water are gradually added, at 40° C. Still at this temperature, the phases are separated by settling, the aqueous phase is removed and the organic phase is then cooled to 15° C. and 500 ml of water and 20 g of glacial acetic acid are added. The phases are separated by settling, the aqueous phase is removed, the organic phase is washed first with water, then with dilute sodium hydroxide and finally again with water, the toluene phase is dried azeotropically and evaporated to dryness under vacuum, and the solid residue is dried under vacuum at 40° C. 345.5 g of 1-benzyl-4-cyano-4-[(N-methyl)benzylamino]piperidine are thus obtained; m.p.=67–68° C.

(b) 330 g of the product obtained at the end of step (a) are added to 2.1 l of a solution of phenylmagnesium bromide in a toluene/methyl tert-butyl ether mixture, obtained from 486.6 g of bromobenzene and 75.32 g of magnesium, and cooled to 15° C. The reaction mixture is left for 2 hours at room temperature, it is then treated with 1.5 l of ice-cold water and 100 ml of aqueous 30% hydrogen peroxide solution for 90 minutes at 2° C, and is left stirring for 30 minutes. The phases are separated by settling, the aqueous phase is removed and the organic phase is washed with water. It is treated with a solution of 70 ml of acetic acid in 765 ml of water to obtain a pH of between 6.5 and 7.5. The organic phase is treated with dilute hydrochloric acid, and the aqueous phase is removed and treated with 1.5 l of n-butanol. Sodium hydroxide is added to pH 14, the phases are separated by settling and the organic phase is washed while hot (60° C.) with water. The aqueous phase is removed and the organic phase is dried azeotropically. This phase is cooled to 70° C., 2.24 l of absolute ethanol are added, followed by addition of a solution of 185 g of oxalic acid in 180 ml of ethanol, and the mixture is refluxed for 1 hour. The resulting mixture is allowed to cool to 20° C. and the precipitate is filtered off and washed with ethanol. 382 g of 1-benzyl-4-(N-methyl)benzylamino-4-phenylpiperidine dioxalate are thus obtained; m.p. 179–180° C.

(c) A mixture of 300 g of the product obtained at the end of step (b), 1.5 l of methanol and 30 g of 5% Pd/C containing 50% water is hydrogenated at 45° C. and at ambient pressure for 24 hours, 300 ml of water are then added thereto and the mixture is refluxed for 30 minutes. The mixture is filtered at this temperature, the methanol is removed by distillation and the essentially aqueous phase is heated to 95° C. 1.7 l of n-butanol are added while maintaining the temperature at 95° C., the mixture is then refluxed and cooled to 20° C., and the precipitate is filtered off, washed with a 9/1 butanol/water mixture (v/v) and dried at 60° C. under vacuum. 144.25 g of 4-methylamino-4-phenylpiperidine sesquioxalate monohydrate are thus obtained; m.p.=252–254° C. (capillary).

What is claimed is:

1. A process for preparing a 4-amino-4-phenylpiperidine of formula (I):

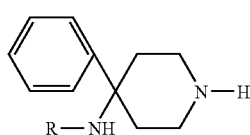

in which R is hydrogen or a $(C_1-C_3)$alkyl group wherein:

(a) a 1-protected 4-piperidone of formula

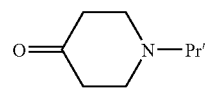

in which Pr' represents a removable N-protecting group, is treated sequentially first with an alkali metal cyanide and then, in the reaction medium containing the cyanohydrin thus obtained, with an amine of formula:

in which E represents a group $R'=(C_1-C_3)$alkyl, or an N-protecting group and Pr" is an N-protecting group, the protecting group(s) being removable under the same conditions as Pr';

(b) the compound thus obtained of formula:

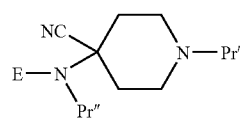

in which Pr', Pr" and E are as defined above, is subjected to a Grignard reaction with a phenylmagnesium halide; and (c) the two or three protecting groups are removed from the compound thus obtained of formula:

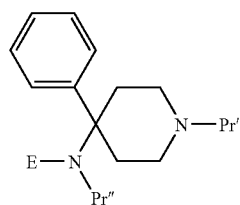

and compound (I) is isolated either in the form of one of its salts, which is converted into the free base, or in the form of the free base, which is converted into one of its salts.

2. The process as claimed in claim 1 for the preparation of a 4-amino-4-phenylpiperidine of formula:

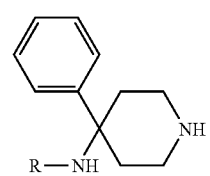

in which R represents a $(C_1–C_3)$alkyl group wherein in step a), treatment is performed with an amine of formula Pr"ENH in which E is a $(C_1–C_3)$alkyl group, and Pr" is as defined in claim 1.

3. The process as claimed in claim 1 wherein the starting reagents used are a compound of formula (II) and a compound of formula (III) in which E represents a group R"=$(C_1–C_3)$alkyl and Pr' and Pr" represent, independently a benzyl radical, which is unsubstituted or substituted on the benzene ring with a halogen, a $(C_1–C_4)$alkyl group or a $(C_1–C_4)$alkoxy group; a benzhydryl radical; or a trityl radical.

4. The process as claimed in claim 1 wherein the starting reagent used is a compound of formula (II) in which Pr' is a benzyl group, and a compound of formula (III) in which Pr" is also a benzyl group.

5. The process as claimed in claim 1 wherein the compound of formula (IV) in which Pr' and Pr" are both a benzyl group is subjected, in step b), to a Grignard reaction with phenylmagnesium bromide.

6. The process as claimed in claim 1 wherein the starting reagent used is a compound of formula (III) in which E is a methyl group.

7. The process as claimed in claim 2 wherein the starting reagents used are a compound of formula (II) and a compound of formula (Ill) in which E represents a group R' = $(C_1–C3)$alkyl and Pr' and Pr" represent, independently, a benzyl radical, which is unsubstituted or substituted on the benzene ring with a halogen, a $(C_1–C4)$alkyl group or a $(C_1–C4)$alkoxy group; a benzhydryl radical; or a trityl radical.

8. The process as claimed in claim 2 wherein the starting reagent used is a compound of formula (II) in which Pr' is a benzyl group, and a compound of formula (III) in which Pr" is also a benzyl group.

9. The process as claimed in claim 3 wherein the starting reagent used is a compound of formula (II) in which Pr' is a benzyl group, and a compound of formula (Ill) in which Pr" is also a benzyl group.

10. The process as claimed in claim 2 wherein the compound of formula (IV) in which Pr' and Pr" are both a benzyl group is subjected, in step b), to a Grignard reaction with phenylmagnesium bromide.

11. The process as claimed in claim 3 wherein the compound of formula (IV) in which Pr' and Pr" are both a benzyl group is subjected, in step b), to a Grignard reaction with phenylmagnesium bromide.

12. The process as claimed in claim 4 wherein the compound of formula (IV) in which Pr' and Pr" are both a benzyl group is subjected, in step b), to a Grignard reaction with phenylmagnesium bromide.

13. The process as claimed in claim 2 wherein the starting reagent used is a compound of formula (III) in which E is a methyl group.

14. The process as claimed in claim 3 wherein the starting reagent used is a compound of formula (III) in which E is a methyl group.

15. The process as claimed in claim 4 wherein the starting reagent used is a compound of formula (III) in which E is a methyl group.

16. The process as claimed in claim 5 wherein the starting reagent used is a compound of formula (III) in which E is a methyl group.

* * * * *